United States Patent
Ara et al.

(10) Patent No.: US 6,509,183 B1
(45) Date of Patent: Jan. 21, 2003

(54) DNA FRAGMENT CONTAINING GENE FOR ALKALINE PULLULANASE

(75) Inventors: Katsutoshi Ara, Oyama; Kazuaki Igarashi, Kaminokawa-machi; Katsuhisa Saeki; Shuji Kawai, both of Kawachi-machi; Susumu Ito, Utsunomiya, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 08/307,589

(22) PCT Filed: Feb. 24, 1994

(86) PCT No.: PCT/JP94/00292

§ 371 (c)(1),
(2), (4) Date: Sep. 28, 1994

(87) PCT Pub. No.: WO94/19468

PCT Pub. Date: Sep. 1, 1994

(30) Foreign Application Priority Data

Feb. 25, 1993 (JP) ............................................. 5-036949
Feb. 26, 1993 (JP) ............................................. 5-038390

(51) Int. Cl.⁷ ............................ C12N 9/44; C12N 9/00; C12N 1/20; C12N 15/00
(52) U.S. Cl. .................... 435/210; 435/183; 435/252.3; 435/320.1; 435/69.1
(58) Field of Search .............................. 435/210, 320.1, 435/252.3, 69.1; 536/23.2

(56) References Cited

U.S. PATENT DOCUMENTS 5,147,796 A 9/1992 Ara et al. ................... 435/210

OTHER PUBLICATIONS

Igarashi et al, *Biosci. Biotech. Biochem.*, 56 (3): 514–516, 1992.
Ara, et al., *Biosci. Biotech. Biochem*, 56 (1): 62–65, 1992.
Sambrook, et al., "Molecular Cloning: A Laboratory Manual", Cold Spring Harbor Press, p. 11.3–11.19, 1989.

*Primary Examiner*—Ponnathapu Achutamurthy
*Assistant Examiner*—Manjunath N Rao
(74) *Attorney, Agent, or Firm*—Oblon, Spivak, McClelland, Maier & Neustadt, P.C.

(57) ABSTRACT

A DNA fragment coding for alkaline pullulanase, which contains about 6.3 Kb base pairs and has a restriction map shown in FIG. 2, a recombinant vector containing the DNA fragment, and a microorganism carrying the vector.

Also disclosed is a method of preparing alkaline pullulanase which comprises culturing a transformant microorganism which has been transformed with a recombinant vector containing a DNA fragment coding for alkaline pullulanase, having a restriction enzyme map shown in FIG. 2 and having about 6.3 Kb base pairs.

According to the method of the invention, alkaline pullulanase which is useful as a component of detergents can be mass-produced in a low cost.

4 Claims, 6 Drawing Sheets

DNA FRAGMENT CONTAINING GENE FOR ALKALINE PULLULANASE

BACKGROUND OF THE INVENTION

1. Field of the Invention

The present invention relates to a DNA fragment containing a gene for alkaline pullulanase derived from an alkalophilic strain of the genus Bacillus to a recombinant vector with said DNA fragment inserted therein., and further to a transformant microorganism transformed with said vector.

The present invention also relates to alkaline pullulanase for use as an effective additive in detergents, which is obtained by a recombinant technique, and to a method of preparing the pullulanase.

2. Description of the Related Art

Pullulanase is an enzyme which cuts specifically the alpha-1,6-glucoside bond present in the molecule of pullulan to generate maltotriose as the major product. This enzyme was first found by Bender and Wallenfels [Biochem. Z., 334, 79, (1961)] in culture of *Aerobacter aerogenes*. Since then, various microorganisms have been reported to produce alkaline pullulanases, which include Bacillus sp. [J. Jpn. Soc. Starch Sci., 30, 200, (1983)], *Bacillus acidopullulyticus* [Agric. Biol. Chem., 52, 2293, (1984)], *Bacillus stearothermophilus* [Eur. J. Appl. Microbiol. Biotechnol., 17, 24, (1983)], *StrePtococcus mitis*[Biochem. J., 10, 33, (1968)], *Lactobacillus*[Starch Science, 28, 72, (1987)], *Clostridium thermohydrosulfuricum*[Appl. Environ. Microb., 49, 5, (1985); Biochem.J., 246, 193, (1987)], Thermus sp. [J. Jpn. Soc. Starch Sci., 34, 1, (1987)], and *Clostridium thermosulfurogenes* [Appl. Microb. Biotechnol., 33, 511 (1990)].

Presently, pullulanase is known to hydrolyze the alpha-1,6-glucoside linkages not only of pullulan, but also of starch, glycogen, amylopectin, and branched oligosaccharides, and is called a "debranching enzyme". This enzyme is also known to produce glucose, maltose and maltooligosaccharides (such as maltotriose, maltotetraose, maltopentaose and maltohexaose), from starch with high yield when used in combination with endo-type amylase and with exo-type amylase. In recent years, therefore, pullulanase is highlighted in starch-manufacturing industry.

Based on the characteristics of the pullulanase, the inventors of the present invention incorporated pullulanase and alpha-amylase into detergents. They discovered that the detergent power of the compositions was markedly enhanced especially against starch soil, and filed a patent application (Japanese Patent Application Laid-open (Kokai) No. 132193/1990).

Enzymatic components of detergents must exhibit their maximal activities in an alkaline pH range, or must be resistant to alkaline washwater. However, almost all pullulanases found hitherto in the natural world are so-called neutral or acid pullulanase, and exhibit their maximal and steady enzymatic activities in the neutral or acidic pH range. There have been found very few alkali-resistant pullulanases which are resistant to alkaline environment. In this specification, the term "alkaline pullulanase" is used for pullulanase having its optimum pH in the alkaline range, and the term "alkali-resistant pullulanase" is used for pullulanase having its optimum pH in the neutral to acidic range while having a sufficient and steady activity in the alkaline pH range when compared with the optimum activity. The term "neutral" indicates a pH range of 6 to 8. The term "alkaline" indicates a pH range higher than the neutral range.

Only two publications have reported a method of producing alkaline or alkali-resistant pullulanases: Horikoshi et al. cultured an alkalophilic strain of the genus Bacillus (Bacillus sp. 202-1) and produced alkaline pullulanase (Japanese Patent Publication (Kokoku) No. 277786/1978); and the inventors of the present invention produced alkaline pullulanase from Bacillus sp. KSM-AP 1876 (Japanese Patent Application Laid-open (Kokai) No. 87176/1991).

The gene for alkaline pullulanase from an alkalophilic Bacillus has not yet been obtained, and therefore, mass-production of the enzyme by genetic engineering and improvement of the enzyme by protein engineering have been difficult to carry out.

SUMMARY OF THE INVENTION

Accordingly, an object of the present invention is to provide a DNA fragment containing gene for alkaline pullulanase derived from an alkalophilic bacterial strain which belongs to the genus Bacillus, to a recombinant vector with said DNA fragment inserted therein, and further to transformant microorganism transformed with said recombinant vectors.

Another object of the present invention is to provide alkaline pullulanase by a genetic approach, and a method of mass-producing alkaline pullulanase by a genetic approach.

Generally speaking, in order to enhance the titer of an enzyme, culture conditions of productive microorganisms are suitably selected, and breeding based on mutation is followed. Breeding by recombinant techniques, which has progressed markedly in recent years, has received attention as it may enable a direct manipulation of the gene. In such breeding by recombinant techniques, it is essential that the alkaline pullulanase gene be isolated. The inventors of the present invention, in an attempt to carry out breeding by recombinant techniques, first prepared a recombinant bacterial strain which belongs to the genus Escherichia and which produces alkaline pullulanase, and isolated therefrom a DNA fragment containing the alkaline pullulanase gene. The obtained DNA fragment was analyzed comparing the gene with other pullulanase genes which have been isolated from various bacterial strains which belong to the genus Bacillus, and as a result, it was revealed that the obtained DNA fragment was a new fragment having a unique restriction enzyme map. The inventors continued their research and succeeded in cloning of the alkaline pullulanase gene by means of gene recombination using chromosome of an alkalophilic bacterial strain which belongs to the genus Bacillus as a starting material, and opened up a way to the mass-production of a new alkaline pullulanase by the use of this gene. The present invention was accomplished based on these findings.

Accordingly, in one aspect of the present invention, there is provided a DNA fragment coding for an alkaline pullulanase which comprises about 6.3 kilo base pairs and has a restriction map shown in FIG. 2, a recombinant vector which contains the DNA fragment, and a recombinant microorganism carrying the recombinant vector.

In another aspect of the present invention, there is provided a method of producing an alkaline pullulanase, which comprises culturing a transformant microorganism transformed with a recombinant vector which contains the above-described DNA fragment, and harvesting alkaline pullulanase from the culture.

The above and other objects, features and advantages of the present invention will become apparent from the following description.

DETAILED DESCRIPTION OF THE INVENTION AND PREFERRED EMBODIMENTS

Figure 1:
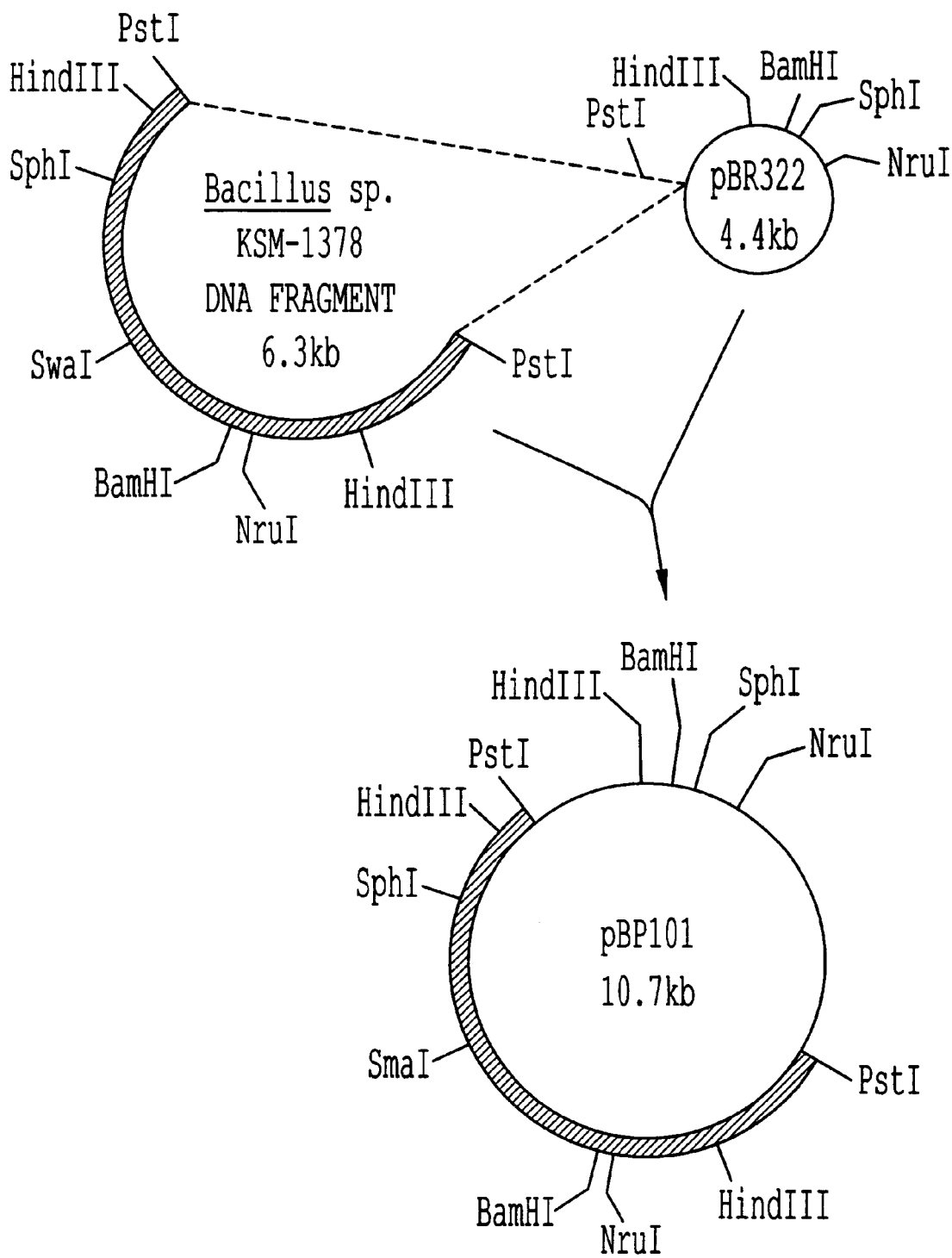
FIG. 1 shows a process of constituting a recombinant plasmid pBP101 using a vector plasmid pBR322. The Pst I fragment of 6.3 Kb shown by a bold line is a segment which contains alkaline pullulanase gene derived from Bacillus sp. KSM 1378.

As the microorganism capable of serving as a donor for alkaline pullulanase gene in the present invention, mention may be given, for example, to Bacillus sp. KSM-1378, an alkalophilic bacterial strain which belongs to the genus Bacillus. This bacterial strain has been isolated by the inventors of the present invention from a soil sample collected in Tochigi-city, Tochigi Prefecture, Japan as a strain capable of producing significant amounts of extracellular alkaline pullulanase Y having alpha-amylase activity, and has been deposited with the Fermentation Research Institute under FERM BP-3048. The taxonomic characteristics of this strain have been described in detail by the present inventors in Japanese Patent Application Laid-open (Kokai) No. 108482/1991, which is hereby incorporated by reference.

The chromosomal DNA can be obtained from the donor bacterial strain by a method proposed by Marmur [J. Mol. Biol., 3, 208, (1961)] or by a method proposed by Saito and Miura [Biochim. Biophys. Acta, 72, 619, (1963)], or by other similar methods.

Once the chromosomal DNA was obtained, cleavage thereof using a restriction enzyme gives a DNA fragment containing the alkaline pullulanase gene. For this purpose, any restriction enzyme may be used as long as it does not have a cleavage site in the gene for alkaline pullulanase. Moreover, if such reaction conditions that will cause only a partial cleavage is employed, any restriction enzymes can be used. Thus, various restriction enzymes can be used according to the conditions und er which the cleavage takes place.

There is no limitation on the host-vector system useful for the gene recombination as long as the gene for alkaline pullulanase can be expressed, and the vector is replicable in the host while stably retaining the inserted gene. For example, EK system in which *Escherichia coli* K-12 strains serve as the host and BM system in which *Bacillus subtilis* Marburg strains serve as the host may be mentioned. Specific examples of the host include HB101, C600 and JM109 strains for the EK system, and BD170 and MI112 strains for the BM system. Concerning the vector, the use of such a vector that is capable of being cleaved at one single site with the restriction enzyme which is used for cleaving the chromosomal DNA is convenient for ligation with the chromosomal DNA fragment. More specifically, in a case in which the chromosomal DNA is cleaved with PstI, vectors pBR322, pUC12 and pUC18 are mentioned for the EK system, and vectors pUB110 and pBD8 are mentioned for the BM system. Other vectors having no cleavage sites available for the restriction enzyme used for cleaving the chromosomal DNA can also be used if a homopolymer ligation method [Nelson, T. and Brutlag, D., Methods in Enzymol., 68, 41, (1980)] or the like is employed upon ligation. Ligation of the above chromosomal DNA fragment with the vector DNA cleaved with the restriction enzyme gives a recombinant plasmid. The ligation is carried out by, for example, a method using a DNA ligase or by a homopolymer ligation method. Examples of the DNA ligase include those of *Escherichia coli* and of T4 phage.

The method of transforming the host microbial strain using the thus obtained recombinant vector is not critical. For example, the calcium chloride method [Mandel, M. and Higa, A., J. Mol. Biol., 53, 159, (1970)] and the rubidium chloride method [Bolivar, F. and Backman, K., Methods in Enzymol., 68, 253 (1979)] may be used for the EK system host strains, and the competent cell method [Contente, S. and Dubnau, D., Mol. Gen. Genet., 177, 459 (1979)] and the protoplast method [Chang, S. and Cohen, S. N., Mol. gen. Genet., 168, 111 (1978)] for the BM system host strains.

No particular limitation is imposed on the method of selecting and isolating a microorganism transformed with alkaline pullulanase gene or with DNA fragment of the donor chromosome which contains alkaline pullulanase gene from the transformant strains. However, it is preferable that a first selection is carried out based on the expression of a marker factor such as antibiotic resistance, and then a second selection is carried out using, as an index, the. alkaline pullulanase activity of the host. Specifically, when pBR322 of the EK system is employed as a vector plasmid, and a Pst I fragment of the chromosomal DNA is inserted into the plasmid at the Pst I site thereof, ampicillin resistance gene containing this cleavage site is inactivated. Therefore, a first selection may be performed using tetracycline resistance as an index because the gene responsible for tetracycline resistance lacks a cleavage site of Pst I. Subsequently, the transformants thus selected are transferred to a properly prepared agar medium containing colored pullulan [Kanno, M. and Tomiura, E., Agric. Biol. Chem., 49, 1529 (1985)] by the replica plating method and cultured. After colonies are emerged, such colonies that form transparent zones around them as a result of decomposing pullulan can be selected as a target transformant.

A recombinant vector of the thus-obtained transformant can be prepared by a conventional plasmid preparation method or a phage preparation method [Maniatis, T. et al., Molecular Cloning, (1982)]. If cleavage patterns of the recombinant vector by the use of various restriction enzymes are analyzed by electrophoresis or like methods, the obtained recombinant vector (recombinant plasmid or recombinant pharge) can be identified as being a ligated product of a vector and a DNA fragment containing alkaline pullulanase gene. The alkaline pullulanase gene according to the present invention is contained in a DNA fragment of about 6.3 Kb, the both ends of which are Pst I cleavage sites as shown in FIG. 1.

Figure 2:
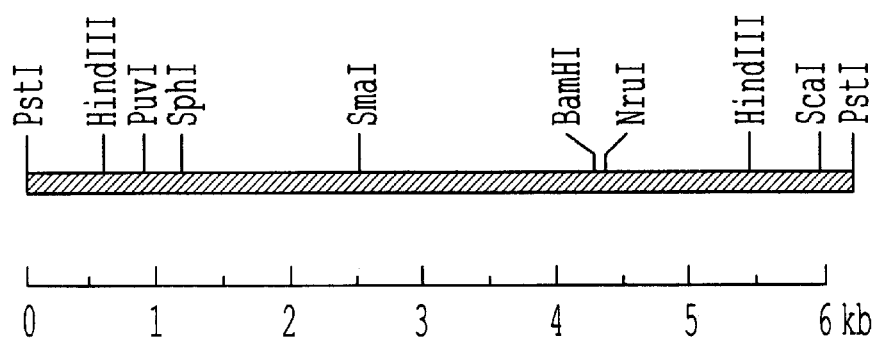
FIG. 2 shows the restriction map of pBP101.

Suitable examples of the recombinant vector containing the alkaline pullulanase gene according to the present invention include recombinant plasmid pBP101 (FIG. 1). This plasmid is an insertion product of about 10.7 Kb which was obtained by inserting a DNA fragment of about 6.3 Kb containing the alkaline pullulanase gene as shown in FIG. 1 into vector plasmid pBR322 at the Pst I cleavage site thereof. The detailed restriction map of the Pst I fragment of the obtained chromosomal DNA is shown in FIG. 2.

In order to culture the transformant, such media and culture conditions that are ordinarily used for the selected host microorganism may be used. Both synthetic and natural media are suitable. Suitable examples of the carbon source include glucose, fructose, maltose, lactose, sucrose and the like. Suitable examples of the nitrogen source include $NH_4Cl$, $(NH_4)_2SO_4$, casamino acid, yeast extract, malt extract, peptone, meat extract, bacto-tryptone, and corn steep liquor. Examples of other nutrition source include $K_2HPO_4$, $KH_2PO_4$, NaCl, $MgSO_4 \cdot 7H_2O$, vitamin $B_1$ and $MgCl_2 \cdot 6H_2O$. The culture is preferably an aerobic spinner culture and carried out at pH 4 to 8, in a temperature range of 28 to 40° C. for 5 to 90 hours.

Collection of the alkaline pullulanase is performed by centrifugally separating cultured cells from the culture broth, washing the separated cells with a buffer solution, and completely lysing the cells by ordianry means such as ultrasonication, a French press method, a glass beads method, or a lysozyme method. By this procedure, a crude enzyme solution is obtained. The thus obtained crude enzyme solution can be purified by such means that are ordinarily employed for purifying enzymes including salting out, dialysis, ion exchange chromatography, gel filtration, chromatography using, for example, hydroxyapatite, and any suitable combinations of these.

As a suitable example of the recombinant microorganism transformed with the recombinant plasmid, *Escherichia coli* HB101(PBP101) is mentioned. It is a strain derived from the strain *Escherichia coli* HB101 by introducing a recombinant plasmid pBP101 thereto. When culturing is carried out in a medium ordinarily used for culturing bacteria of the genus Escherichia, for example an LB medium, alkaline pullulanase can be produced.

A method of collecting alkaline pullulanase from the cells of microorganism is described below.

Cells harvested from the obtained culture were suspended in Tris-HCl buffer (pH8.0), disrupted by ultrasonication, and then centrifugally separated. Pellet was removed to obtain a supernatant. The supernatant was added with ammonium sulfate so that 80% saturation was obtained, and pullulanase contained in the supernatant is completely precipitated. Subsequently, dialysis was carried out using a 10 mM Tris-HCl buffer (pH 9.0), and adsorption was allowed to take place on a DEAE-Toyopearl 650s column equilibrated with the same buffer. Elution was performed using a 10 mM Tris-HCl buffer (9.0) from the concentration gradient of 0 to 1 M NaCl. Active fractions were coll ected and condensed using a ultrafiltration membrane having an average fractional molecular weight of 10,000, then dialysed against a 10 mM Tris-HCl buffer (pH 9.0) containing 0.1 M NaCl overnight. Thereafter, via adsorption on a Sephacryl S-200 column equilibrated with a 10 mM Tris-HCl buffer (pH 9.0) containing 0.1 M NaCl and elution using the same buffer containing 0.1 M NaCl, active fractions are obtained. The thus obtained purified enzyme gave a single band in poly- acrylamide gel electrophoresis (gel: 10%) and sodium dodecyl sulfate electrophoresis (gel: 10%). Yield of the active fractions was about 4%.

The enzymatic characteristics of the thus-obtained alkaline pullulanase of the present invention are described below.

Measurement of the enzymatic activity was performed using the following buffers (each in 10 mM):

pH 4–6: Acetic acid buffer
pH 6–8: Tris-HCl buffer
pH 8–11: Glycine-NaCl-NaOH buffer
pH 11–12: KCl-NaOH buffer.

The process of measurement was as follows:

A substrate solution (0.9 ml) obtained by dissolying pullulan in each buffer (ultimate pullulan concentration in the reaction system: 0.25%) was added with an enzyme solution (0.1 ml) and allowed to react at 50° C. for 30 minutes. After the reaction, amounts of reducing sugar were quantitatively determined by a 3,5-dinitrosalicylic acid (DNS) method: 1.0 ml of a DNS reagent was added to 1.0 ml of the reaction solution and the mixture was heated for developing color for 5 minutes at 100° C. It was then cooled down and diluted with 4.0 ml of deionized water. Quantitative determination was performed by colorimetry at a wave length of 535 nm. The enzymatic titer was indicated by unit; 1 unit (1U) of the enzymatic titer was defined to be the amount of enzyme which produces, in 1 minute, reducing sugar equivalent to 1 micromole of glucose.

Ezymatic Properties

1) Action:

Hydrolyze pullulan and amylopectin acting at the alpha-1,6-glucoside bond. The present enzyme also hydrolyzes starch and partial decomposition products thereof at the alpha-1,6-glucoside bond as shown in Table 1.

TABLE 1

| Substrate | Concentration (%) | Relative Activity (%) |
|---|---|---|
| Pullulan | 0.25 | 100.0 |
| Glycogen (oyster) | 0.25 | 0 |
| Glycogen (rabbit liver) | 0.25 | 0 |
| Amylopectin (potato) | 0.25 | 22.1 |
| Amylose | 0.25 | 0 |

2) Working pH and Optimum pH:

Works in the pH range of 6.5 to 10.5, with the optimum pH range of 8.5 to 9.5. In the pH range of 7.5 to 10.0, relative activity of not less than 40% activity of the activity in the optimum pH range was observed.

Figure 3:
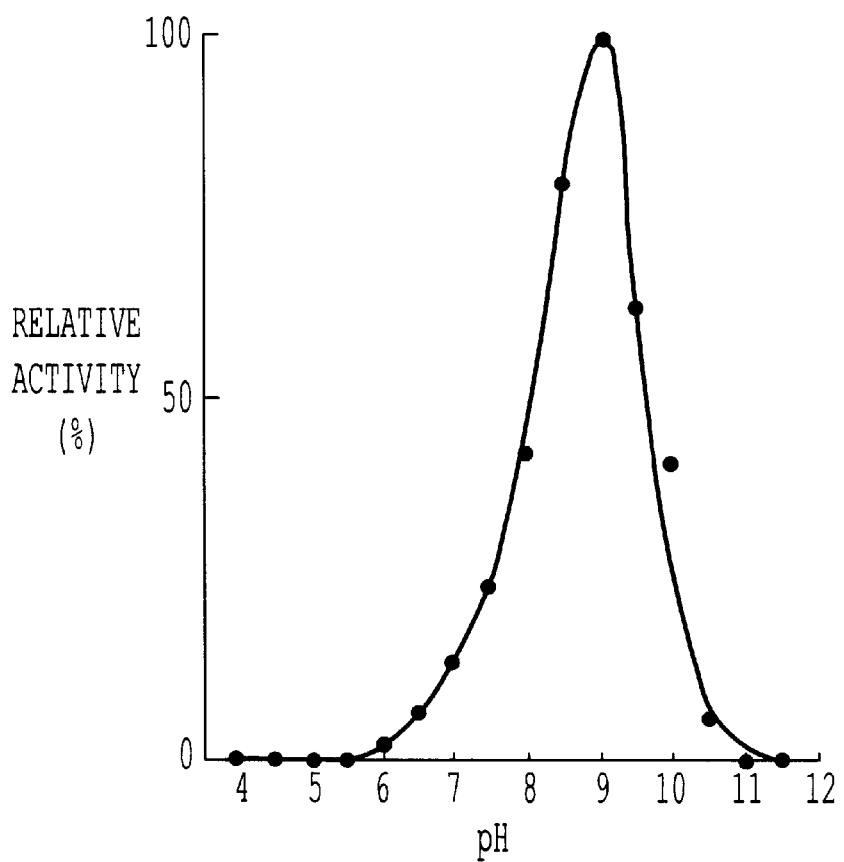
FIG. 3 shows the relation between the pH (working pH and optimum pH) and the activity of the pullulanase produced by a recombinant strain, *Escherichia coli* HB101 (pBP101).

The activity of alkaline pullulanase is shown in FIG. 3. The measurement was performed using a reaction system containing 0.25% pullulan and 10 mM acetic acid buffer (for pH 4–6), Tris-HCl buffer (for pH 6–8), glycine-NaCl-NaOH buffer (for pH 8–11) or KCl-NaOH buffer (for pH 11–12) and allowing the enzyme to react at 50° C. for 30 minutes.

3) pH Stability:

Very stable in the range of pH 6.0 to 10.0. In the pH range of 5.5 to 10.5, about 30% or higher activity was retained.

Figure 4:
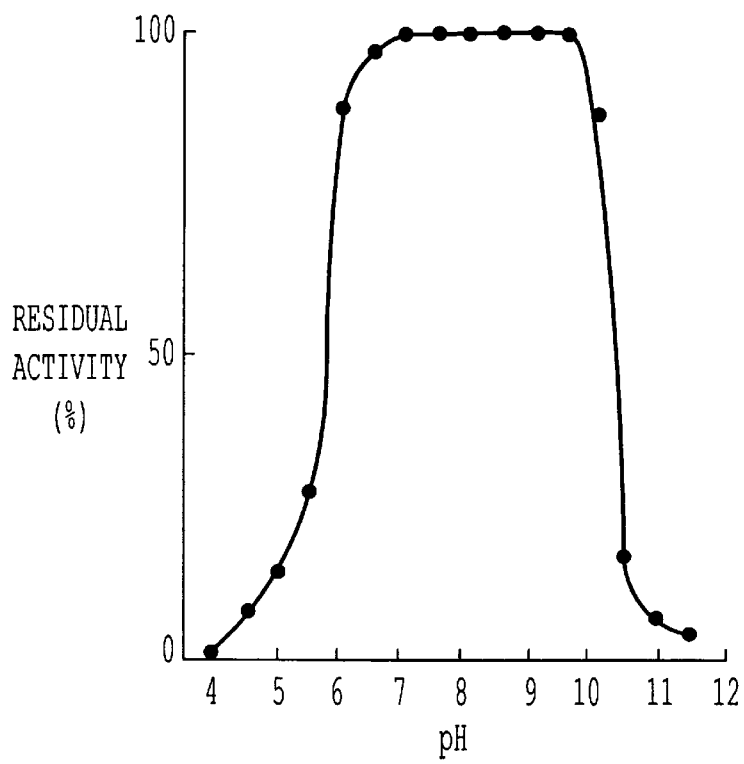
FIG. 4 shows the pH stability of the activity of the alkaline pllulanase produced by a recombinant strain, *Escherichia coli* HB101 (pBP101).

FIG. 4 shows the pullulanase activity measured under various pH conditions. The measurement was performed using a reaction system containing 0.25% pullulan and 10 mM acetic acid buffer (for pH 4–6), Tris-HCl buffer (for pH 6–8), glycine-NaCl-NaOH buffer (for pH 8–11) or KCl-NaOH buffer (for pH 11–12) and allowing the enzyme to react at 50° C. for 10 minutes.

Figure 5:
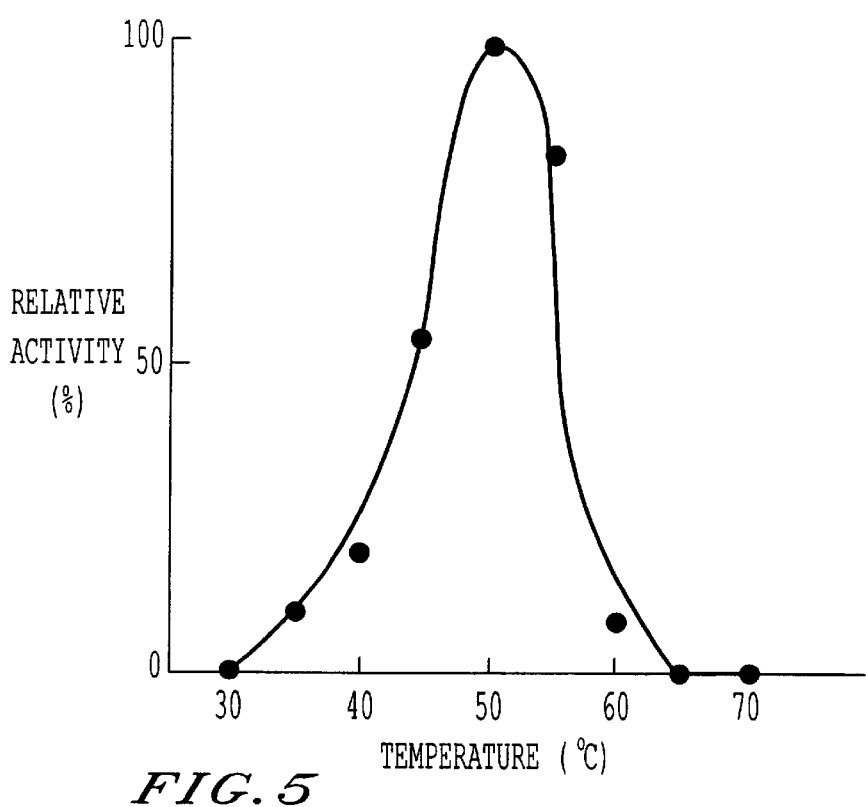
FIG. 5 shows the relation between the temperature (working temperature and optimum temperature) and the activity of the alkaline pullulanase produced by a recombinant strain, *Escherichia coli* HB101 (pBP101).

4) Working temperature and optimum working temperature:

Works in a wide temperature range of 35 to 60° C. The optimum working temperature was observed at about 50° C. (FIG. 5).

Figure 6:
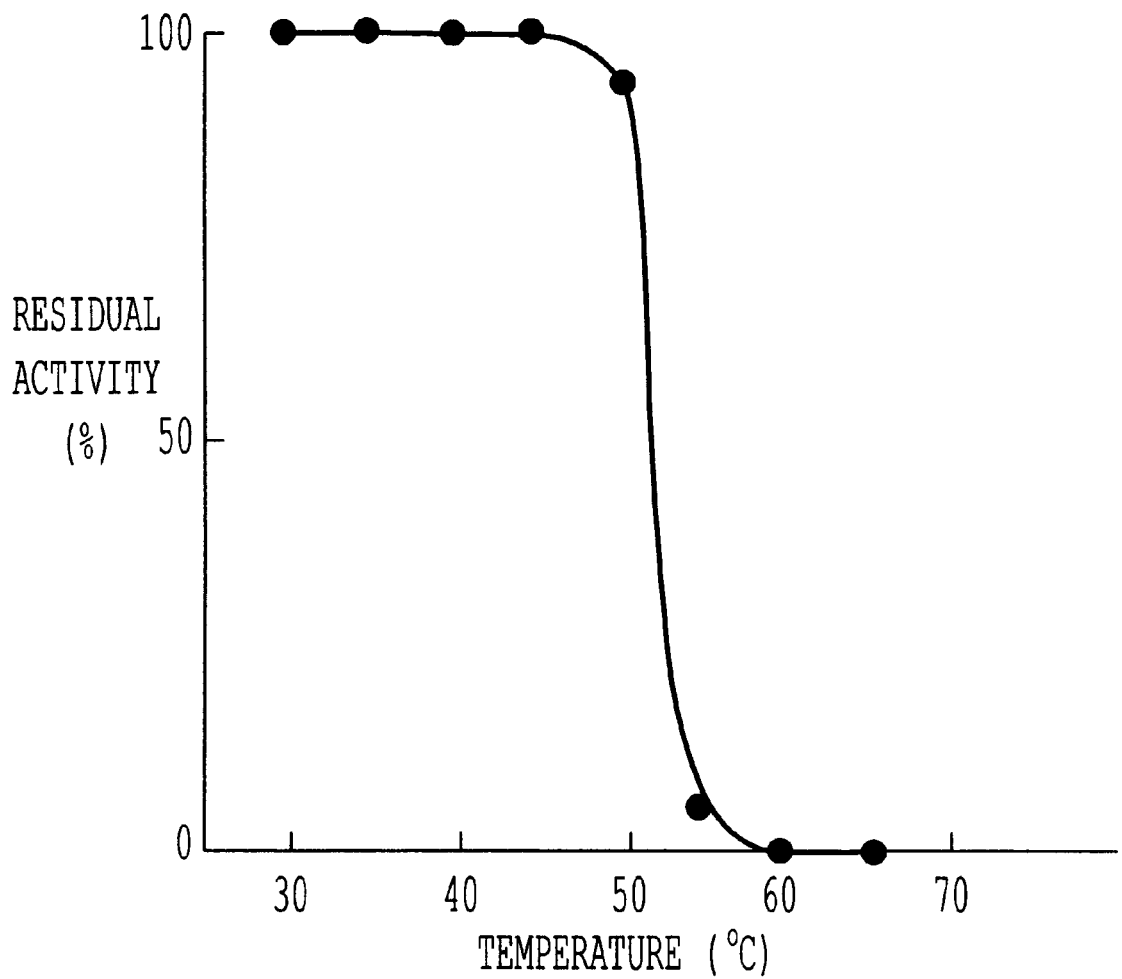
FIG. 6 shows the temperature stability of the alkaline pullulanase produced by a recombinant strain, *Escherichia coli* HB101 (pBP101).

5) Temperature stability:

Under the conditions of pH 9.0 and treatment for 30 minutes at various temperatures revealed that the present enzyme was very stable up to 50° C. (FIG. 6).

6) Molecular weight:

115,000 ±5,000 as judged by sodium dodecyl sulfate electrophoresis.

7) Effects of metal ions:

Activity was strongly inhibited in the presence of 1 mM $Hg^{2+}$ and $Cd^{2+}$, and weakly inhibited by $Zn^{2+}$.

8) Effects of surfactants:

Treatment in a 0.05% solution of various surfactants (for example, sodium salt of alkyl sulfate (AS), sodium salt of polyoxyethylene alkyl sulfate (ES), sodium alpha-olefinsulfonate (AOS), sodium alpha-sulfonated aliphatic ester (alpha-SFE), sodium alkylsulfonate (SAS), SDS, soap and softanol) at 50° C. for 15 minutes hardly affected the enzymatic activity.

9) Effects of chelating agents:

Various chelating agents (EDTA (10 mM), EGTA (10 mM), citric acid (0.05%) and zeolite (0.05%)) hardly affected the enzymatic activity.

As described above, the alkaline pullulanase according to the present invention has the optimum pH in an alkaline pH range of pH 8.5–9.5. When compared with conventional pullulanase, it is noted that the present enzyme has the optimum activity in the range shifted to more alkaline side. Moreover, the optimum temperature is 50° C. and the thermal stability is secured up to 50° C. Furthermore, the enzymatic activity is hardly inhibited in the presence of detergent components such as surfactants and chelating agents. Therefore, the enzyme of the present invention is useful as a component of detergent compositions and has a lot of significance in industry. It is also noted that the present invention succeeded in the mass-production of alkaline pullulanase on a steady basis.

EXAMPLES

The present invention will now be described by way of examples, which should not be constructed as limiting the invention.

Example 1

In order to prepare chromosomal DNA from Bacillus sp. KSM-1378 (FERM BP-3048) which is an alkalophilic bacterial strain belonging to the genus Bacillus and which produces alkaline pullulanase, the strain was grown with shaking in a 200 ml solution containing the medium I below at 30° C. for 30 hours.

TABLE 2

| Medium I (pH 10.0) | |
|---|---|
| Components | % by weight |
| Pullulan | 0.5 |
| Soluble starch | 0.5 |
| Tryptone | 0.2 |
| Yeast extract | 0.1 |
| $KH_2PO_4$ | 0.03 |
| $(NH_4)_2SO_4$ | 0.1 |
| $MgSO_4.7H_2O$ | 0.02 |
| $CaCl_2.2H_2O$ | 0.02 |
| $FeSO_4.7H_2O$ | 0.001 |
| $MnCl_2.4H_2O$ | 0.0001 |
| $Na_2CO_3$ | 0.5 |

After harvesting the cells, a method proposed by Saito and Miura [Biochim. Biophys. Acta, 72, 619 (1963)] was followed to obtain about 2 mg of a purified DNA.

Example 2

10 micrograms of the chromosomal DNA obtained in Example 1 and 1.5 micrograms of vector plasmid pBR322 (Boehringer Mannheim) were separately dissolyed in a solution containing 10 mM Tris-HCl buffer (pH 7.5), 5mM of $MgCl_2$. $6H_2O$, 100 mM of NaCl and 1 mM of 2-mercaptoethanol, to which 10 units of a restriction enzyme, Pst I (Boehringer Mannheim), was added and allowed to react at 37° C. for 2.5 hours. The plasmid pBR322 was further treated with alkaline phosphatase to remove 5'-phosphoric residue. After completion of the reaction, the restriction enzyme was removed by treatment with phenol, followed by precipitation with ethanol. The obtained DNA precipitate and the cleaved vector plasmid pBR322 were dissolyed in 50 microliters of the ligation mixture containing 20 mM of Tris-HCl buffer (pH 7.5), 10 mM $MgCl_2$. $6H_2O$, 10 MM dithiothreitol and 1 mM ATP. Two units of T4 DNA ligase (Boehringer Mannheim) was added to the solution, and the reaction was carried out at 16° C. for 16 hours, whereby the chromosomal DNA fragment and the vector plasmid were ligated.

Example 3

The recombinant plaspnid constructed in Example 2 was used to transform Escherichia coli by the calcium chloride method [Mandel, M. and Higa, A., J. Mol. Biol., 53, 159 (1970)]. The host strain used was Escherichia coli HB101 ($F^-$ hsdS20 recA13 ara-14 proA2 lacY1 galK2 rpsL20 xyl-5 metl-1 supE44 leuB6 thi-1). The cell suspension which has undergone transformation treatment was spread onto an LB agar medium [1.0% trypton (Difco), 0.5% yeast extract (Difco), 0.5% NaCl, 1.5% agar (Wako Pure Chemical)] containing 20 microgramsml of tetracycline (Sigma) and incubated at 37° C. for 24 hours. About 10,000 transformant that had appeared were transferred to an LB agar medium added with tetracycline and propagated by the replica plating method. Thereafter, agar containing 0.2% pullulan, 0.8% red pullulan [Kanno, M. and Tomiura, E., Agric. Biol. Chem., 49, 1529 (1985)] and 1 mg/ml lysozyme was superposed thereon and allowed to react at 37° C. for 5 hours. By the use of colored pullulan simplified method, the strain which contains the target alkaline pullulanase gene forms transparent zones around the colonies thereof. Thus, 1 strain of clone having ability of producing alkaline pullulanase was obtained.

Example 4

The transformant strain obtained in Example 3 was inoculated into an LB liquid medium added with tetracycline and cultured at 37° C. overnight. Thereafter, the culture was transferred to 500 ml of M9CA medium [0.6% $Na_2HPO_4$, 0.3% $KH_2PO_4$, 0.05% NaCl, 0.1% $NH_4Cl$, 0.2% casamino acid (Difco), 2mM $MgSO_4$. $7H_2O$, 0.2% glucose, 20 microgramsml tetracycline] and shake culture was performed at 37° C. for 4 to 5 hours. Then 170 mg of chloramphenicol was added and shake culture was further performed at 37° C. for 15 hours. Cells were harvested from the culture by centrifugation, and the recombinant plasmid was prepared by the method of Maniatis et al. [Maniatis, T et al., Molecular Cloning (1982)] which is a combination of the alkaline lysis method [Birnboim, H. C. and Doly, J., Nucleic Acids Res., 7, 1513 (1979)] and the $CsCl_2$-ethidium bromide density gradient centrifugation method [Radloff, R., Bauer, W. and Vinograd, J., Proc. Natl. Acad. Sci. U.S.A., 57, 1514 (1967)] (FIG. 1).

In order to carry out a detailed analysis, the cleavage pattern analysis was carried out by agarose gel electrophoresis after various restriction enzymes were acted on the plasmid. Based on the result obtained therefrom, a restriction enzyme map was obtained (FIG. 2). It was revealed that the present plasmid was a new plasmid having a restriction enzyme map different from the genes of conventionally known pullulanase species such as a *Bacillus stearothermophilus* heat resistant pullulanase (Japanese Patent Application Laid-open (Kokai) No. 23872/1990). The present plasmid was named pBP101 and the *Escherichia coli* HB101-derived transformant carrying pBP101 was named *Escherichia coli* HB101(pBP101).

Example 5

*Escherichia coli* HB101(pBP101) was cultured in an LB liquid medium added with tetracycline. Cells were harvested, suspended in Tris-HCl buffer (pH 8.0) and disrupted by sonication. Centrifugal separation was effected to remove pellet and the supernatant was obtained as a cell-free extract. Similar procedure was followed to prepare a cell-free extract on HB101(pBR322) strain as control. The pullulanase activity was measured on these two extracts, in such a manner that 0.9 ml of a substrate solution containing pullulan (ultimate concentration: 0.25%) and 40 mM glycine-NaCl-NaOH buffer (pH9.0) as dissolyed was added with 0.1 ml of a solution containing the enzyme, and allowed to react at 40° C. for 30 minutes, and then reducing sugar was quantitatively determined by the aforementioned DNS method. As a result, alkaline pullulanase activity was observed in the cell-free extract of the strain HB101 (pBP101) as shown in Table 3.

TABLE 3

| Bacterial strain | Amount of growth ($OD_{600}$) | Pullulanase activity ($X10^{-3}$ Unit/mg protein) |
|---|---|---|
| Escherichia coli HB101 (pBP101) | 6.8 | 69.1 |
| Escherichia coli HB101 (pBR322) | 7.8 | 1.0 |

Example 6

The cell-free extract obtained in Example 5 was used and crude pullulanase produced was purified by (1) ammonium sulfate-precipitation method (80% saturation), (2) chromatography on a column DEAE Toyopearl 650S (Toyo Soda), and (3) chromatography on a column Sephacryl S200 (Pharmacia) to obtain a purified alkaline pullulanase.

Figure 7:
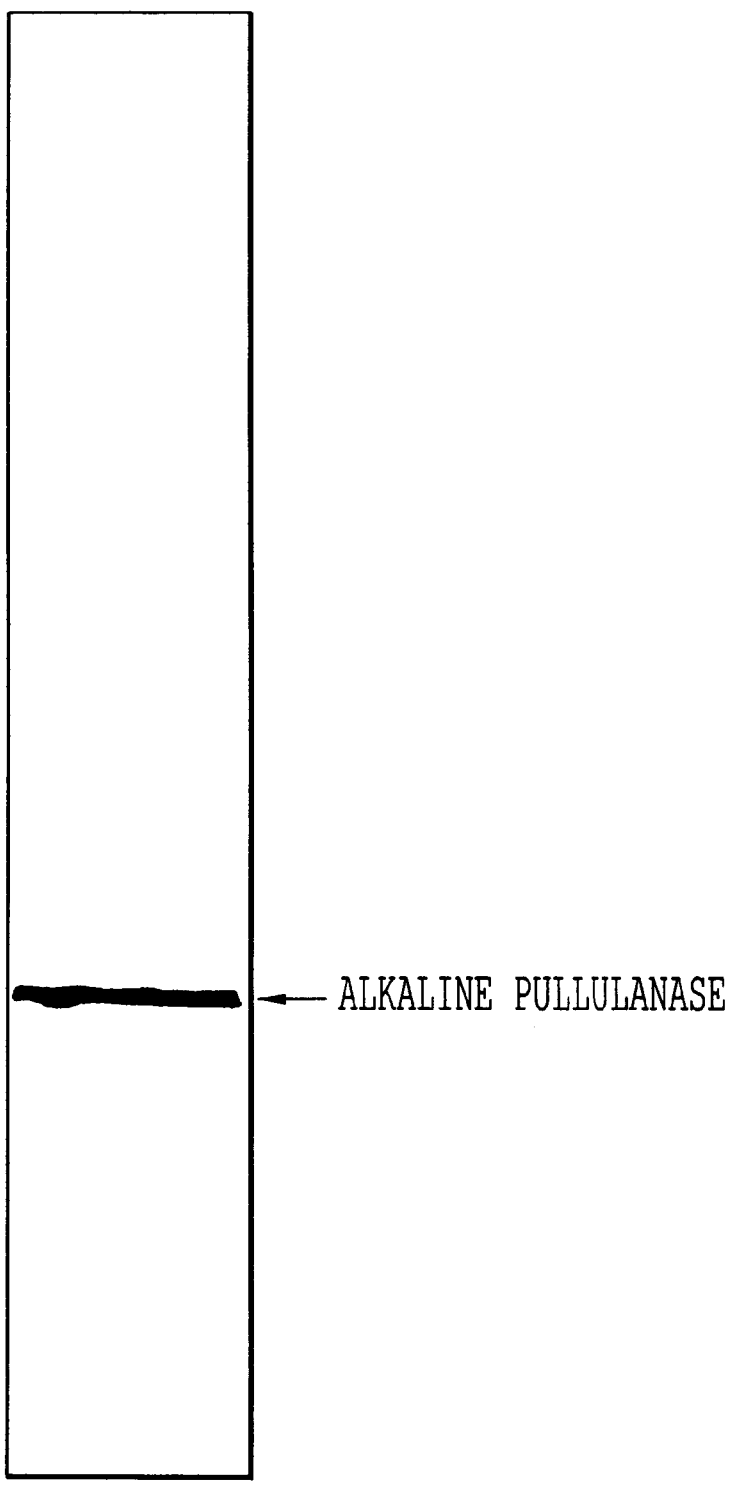
FIG. 7 is a profile of electrophoresis of the alkaline pullulanase produced by a recombinant strain, *Escherichia coli* HB101 (pBP101).

The obtained alkaline pullulanase was subjected to electrophoresis according to the method of Davis [Davis D. J., Ann. N.Y. Acad. Sci., 121, 404 (1964)], and then stained with quick CBB (Wako Pure Chemical). As a result, it was confirmed to give a single protein band (FIG. 7).

Example 7

Figure 8:
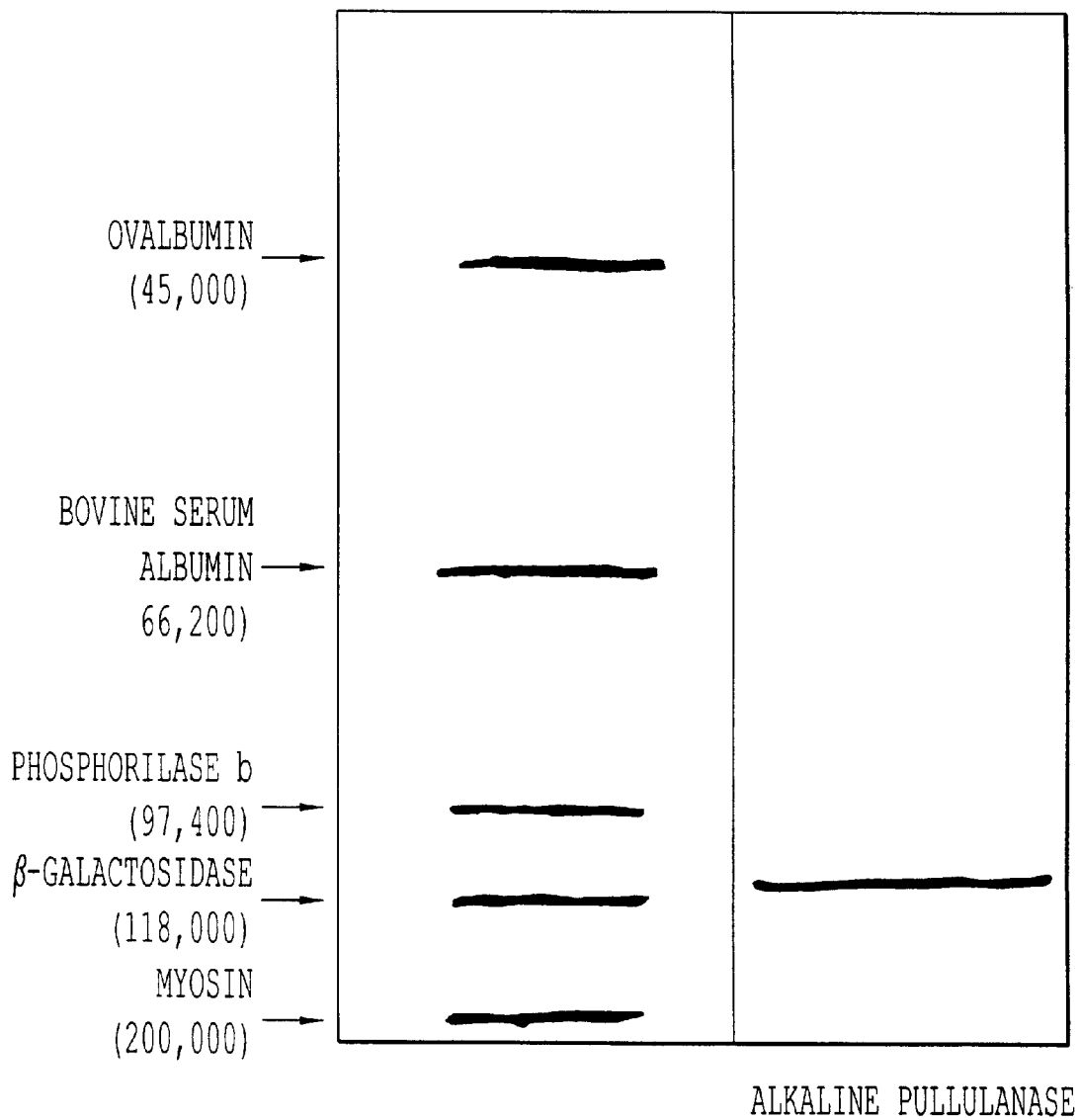
FIG. 8 is a profile of sodium dodecyl sulfate electrophoresis of the alkaline pullulanase produced by a recombinant strain, *Escherichia coli* HB101 (pBP101).

SDS electrophoresis was performed using the alkaline pullulanase obtained in Example 6 in a conventional manner (FIG. 8). As a result, the present enzyme was confirmed to have a molecular weight of 115,000 ±5,000.

Example 8

The optimum pH of the produced pullulanase was measured using the crude enzyme obtained in Example 6. It was found that the pullulanase of the present invention had the optimum working activity at pH 9.2 (FIG. 3). Moreover, the purified enzyme was confirmed to have the aforementioned enzymological characteristics.

What is claimed is:

1. An isolated DNA fragment coding for an alkaline pullulanase which comprises about 6.3 Kb base pairs and has a restriction map as shown in FIG. 2, and which is isolated from Bacillus KSM 1378.

2. A recombinant vector containing the DNA fragment as defined in claim 1.

3. A microorganism carrying the recombinant vector as defined in claim 2.

4. A method of preparing alkaline pullulanase which comprises culturing a transformed microorganism which has been transformed with a recombinant vector containing a DNA fragment coding for alkaline pullulanase, having the restriction map shown in FIG. 2 and having about 6.3 Kb base pairs, and which is isolated from Bacillus KSM 1378; and collecting alkaline pullulanase from the culture.

* * * * *